(12) United States Patent
Carthey et al.

(10) Patent No.: US 10,239,803 B2
(45) Date of Patent: Mar. 26, 2019

(54) PROCESS FOR THE PREPARATION OF VINYL CHLORIDE

(71) Applicant: JOHNSON MATTHEY PUBLIC LIMITED COMPANY, London (GB)

(72) Inventors: Nicholas Andrew Carthey, Berkshire (GB); Andrew George Hiles, London (GB); Joost Johannes Smit, London (GB)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/574,208

(22) PCT Filed: May 26, 2016

(86) PCT No.: PCT/GB2016/051533
§ 371 (c)(1),
(2) Date: Nov. 15, 2017

(87) PCT Pub. No.: WO2016/189318
PCT Pub. Date: Dec. 1, 2016

(65) Prior Publication Data
US 2018/0118643 A1     May 3, 2018

(30) Foreign Application Priority Data

May 27, 2015    (GB) .................................. 1509019.4

(51) Int. Cl.
| | | |
|---|---|---|
| C07C 17/08 | (2006.01) | |
| C07C 17/25 | (2006.01) | |
| B01J 21/18 | (2006.01) | |
| B01J 23/44 | (2006.01) | |
| B01J 23/52 | (2006.01) | |

(52) U.S. Cl.
CPC ............... *C07C 17/25* (2013.01); *B01J 21/18* (2013.01); *B01J 23/44* (2013.01); *B01J 23/52* (2013.01); *C07C 17/08* (2013.01)

(58) Field of Classification Search
CPC ............................... C07C 17/25; C07C 17/08
See application file for complete search history.

(56) References Cited

U.S. PATENT DOCUMENTS

| 4,207,267 A | 6/1980 | Schindler |
|---|---|---|
| 4,482,770 A | 11/1984 | Schmidhammer et al. |

FOREIGN PATENT DOCUMENTS

| BE | 524001 A | * | 5/1954 | ............. C07C 17/25 |
|---|---|---|---|---|
| CN | 103221128 A | | 7/2013 | |
| CN | 104326865 A | | 2/2015 | |
| EP | 0565789 A1 | | 10/1993 | |
| FR | 1110167 A | | 2/1956 | |
| GB | 801663 | | 9/1958 | |
| GB | 2007522 A | | 5/1979 | |
| RU | 2250891 C1 | | 4/2005 | |
| WO | WO-0029359 A1 | * | 5/2000 | ............. C07C 17/25 |
| WO | WO2010055341 A2 | | 5/2010 | |
| WO | WO2011048361 A1 | | 4/2011 | |
| WO | WO2013008004 A2 | | 1/2013 | |

OTHER PUBLICATIONS

BE524001A, May 3, 1954, p. 1-3; English translation (Year: 1954).*
GB1509019.4, UK Search Report under Section 17(5) dated Feb. 22, 2016.
GB1609356.9 UK Combined Search and Examination Report under Section 17 and 18(3) dated Mar. 10, 2017.
Bangladesh Patent Application No. 107/2016, Examination Report dated May 31, 2017.
PCT/GB2016/051533, International Search Report dated Aug. 24, 2016.
PCT/GB2016/051533, Written Opinion dated Aug. 24, 2016.

* cited by examiner

*Primary Examiner* — Medhanit W Bahta
(74) *Attorney, Agent, or Firm* — Baker & Hostetler LLP

(57) ABSTRACT

A process for the production of vinyl chloride comprises the step of passing a feed stream comprising ethylene dichloride (EDC) over a catalyst system comprising a dehydrochlorination catalyst and a hydrochlorination catalyst at a temperature, which may be in the range 150-350° C., sufficient to effect dehydrochlorination of the ethylene dichloride to produce vinyl chloride.

16 Claims, No Drawings

PROCESS FOR THE PREPARATION OF VINYL CHLORIDE

CROSS-REFERENCE TO RELATED APPLICATIONS

This application is the National Stage of International Patent Application No. PCT/GB2016/051533 filed May 26, 2016, which claims priority from Great Britain Patent Application No. 1509019.4 filed May 27, 2015, the disclosures of each of which are incorporated herein by reference in their entireties for any and all purposes.

The present invention concerns the production of vinyl chloride (chloroethene, $H_2C=CHCl$), in particular by thermal or catalytic cracking of ethylene dichloride.

Vinyl chloride is a commercially important chemical feedstock used primarily as a monomer for the production of poly(vinylchloride) (PVC). It is frequently referred to as vinyl chloride monomer (VCM). VCM may be manufactured by different processes. One commercial process includes the dehydrochlorination of 1,2-ethylene dichloride (EDC). The dehydrochlorination may be achieved by thermal "cracking" in which EDC is reacted at a high temperature, usually above 500° C. and at elevated pressure, for example about 12 bar G, to form VCM, HCl and by-products including acetylene, coke and heavier products. This process is endothermic and therefore energy intensive. The conversion is typically about 55% and so it is usually operated with a significant recycle, requiring further energy input. An alternative process involves the catalytic cracking of EDC to form VCM. This process feeds EDC and hydrogen over a catalyst comprising palladium on a carbon support at a temperature of at least 250° C. to form VCM, HCl and some acetylene and ethylene. A conversion of up to about 60% was achieved at a selectivity of >95%. This process is described in WO00/29359, which explains that the hydrogen is present to convert, in situ, any acetylene by-product to ethylene, which can be recycled to form EDC. The conversion of acetylene avoids the build-up of coke which reduces the lifetime of the catalyst. Catalytic cracking is also less energy intensive than thermal cracking. It is an object of the present invention to provide an alternative process for the production of VCM.

According to the invention, a process for the production of vinyl chloride comprises the step of passing a feed stream comprising ethylene dichloride (EDC) over a catalyst system comprising a dehydrochlorination catalyst and a hydrochlorination catalyst at a temperature sufficient to effect dehydrochlorination of the ethylene dichloride to produce vinyl chloride.

Although hydrogen may be present in the feed stream, it is a particular advantage of the process of the invention that hydrogen need not be present. The previously known processes involving thermal cracking or catalytic cracking of EDC both require a hydrogen feed to convert unwanted acetylene to ethylene. In one embodiment of the invention, the feed stream contains EDC and hydrogen at a molar ratio of less than 1 EDC:0.1 $H_2$ (i.e. 1 EDC:<0.1 $H_2$) in particular less than 1:0.001 (i.e. 1 EDC:<0.001 $H_2$). In another embodiment the feed stream contains essentially no hydrogen. In this embodiment, no hydrogen is added to the feed stream. By "essentially no hydrogen" we mean that hydrogen is not added to the feed stream but may be present at a low level as an impurity.

EDC, as used herein, means 1,1-ethylene dichloride and/ or 1,2-ethylene dichloride. Ethylene dichloride for use as a feed stream to a process for making VCM may be made by reacting ethylene with chlorine and/or hydrogen chloride (HCl) in a chlorination or oxychlorination process. Such processes are known, widely practiced commercially and are not included directly in the process of the invention. The EDC produced by such a process is predominantly 1,2-ethylene dichloride (1,2-EDC). 1,2-EDC is the most common feedstock for making VCM from EDC. 1,1-EDC may be present in the feed stream of the process of the invention. 1,1-EDC may be formed as a by-product in a process for making VCM from acetylene in a hydrochlorination process. In an acetylene-based VCM process a typical heavy by-product stream consists of approximately 90% 1,1-EDC and approximately 10% other chlorinated hydrocarbons. The feed stream of the process of the present invention may comprise at least a portion of such a by-product stream. The feed stream of the process of the present invention may comprise at least a portion of a product stream containing EDC formed in a process for the hydrochlorination of acetylene. Dehydrochlorination of the heavy stream may produce VCM, and HCl which can be recycled into the hydrochlorination process. Part of the heavy stream can be purged to prevent build-up of unconvertible heavies in the process. The unconvertible heavies can for example be sent to a thermal or catalytic oxidizer for destruction. Integration of the process of the invention into a process for the manufacture of VCM from acetylene increases the yield of VCM from such a process.

The feed stream may comprise a diluent or inert compound, such as nitrogen, for example. The feed stream may comprise other compounds, including compounds present in the product stream, such as acetylene, ethylene, hydrogen chloride or VCM. The feed stream may contain small amounts (usually less than 1% by weight) of impurities such as HCl, $O_2$, ethylene, $Cl_2$, $CO_2$, VCM, ethylchloride, chloroprene, chloroform, carbon tetrachloride, benzene, trichlorethylene, trichloroethane and heavier chlorinated hydrocarbons. Typically the feed stream is treated to remove at least a portion of such compounds.

The feed stream comprising ethylene dichloride preferably comprises at least 10% by weight of EDC. More preferably the feed stream comprising ethylene dichloride comprises at least 30% by weight of EDC. The feed stream comprising ethylene dichloride may comprise at least 50% by weight of EDC. The feed stream to the process may generally comprise at least 70% by weight of EDC, and may comprise at least 80% EDC. In an embodiment of a commercial process which is a once-through process, the feed stream may comprise 95-100 wt % EDC. When the EDC has been purified, the feed stream may comprise at least 99 wt % EDC. A commercial process may use a purified EDC feed stream but also co-feed a recycle stream. The recycle stream may be taken, for example, from a purification section downstream of an EDC catalytic cracking reactor. Alternatively, the feed stream may comprise EDC and a co-fed stream containing acetylene. When purified acetylene is co-fed with purified EDC in a sufficient amount to react with the HCl produced in the dehydrochlorination of EDC, the theoretical amounts of acetylene and EDC in such a stream would be 21 wt % acetylene and 79 wt % EDC.

In a preferred embodiment, the process of the invention is a process comprising the on-purpose catalytic cracking of EDC to form VCM for the commercial production of VCM. Without wishing to be bound by theory, the hydrochlorination catalyst is believed to catalyse the reaction of acetylene and HCl, (which are both formed as by-products of the dehydrochlorination of EDC in reaction 2 below), to form vinyl chloride. In this way, VCM is formed by reactions 1 and 3 below:

$$CH_2ClCH_2Cl \rightarrow H_2C=CHCl+HCl \quad (1)$$

$$H_2C=CHCl \rightarrow HC\equiv CH+HCl \quad (2)$$

$$HC\equiv CH+HCl \rightarrow H_2C=CHCl \quad (3)$$

The process of the invention therefore may avoid or reduce the requirement to recycle a product stream containing acetylene or ethylene, thereby reducing the overall cost of the process. The process of the invention may be operated as a single-pass process. If required, a portion of the product stream may be recycled.

In one embodiment, acetylene may be present in the feed stream. In such a process, the acetylene may react with HCl in a hydrochlorination reaction to form vinyl chloride. This reaction is exothermic. The heat generated in this reaction may be used to provide heat to the endothermic dehydrochlorination reaction in which the EDC is dehydrochlorinated to produce VCM and HCl. The amount of acetylene present in the feed stream may be balanced so as not to significantly exceed the molar ratio of acetylene:EDC of 1:1. The presence of excess acetylene in the reactor may lead to deactivation of the dehydrochlorination catalyst.

The reaction takes place in the gas phase. Typical temperatures used in the reaction are in the range in the range from 150-350° C., more usually 250-300° C. Typical pressures are in the range from 0 to 55 bar G, more usually about 5 to 15 bar G. In one embodiment of the process, the operating pressure may be 20-55 barg, for example 30-40 barg. Operation of the process at a relatively high pressure (above 30 barg) potentially offers a number of advantages. Such advantages include a smaller reactor and catalyst volume and more efficient heat transfer. A high operating pressure also enables a downstream purification process to be operated at a higher pressure. Operating the downstream purification process at higher pressure can shift the required refrigerant to a higher temperature level, resulting in a lower electrical power requirement.

The dehydrochlorination catalyst is a catalyst which is active for the dehydrochlorination of EDC to produce VCM. A suitable dehydrochlorination catalyst is a supported noble metal catalyst, i.e. a catalyst containing at least one of platinum, palladium, rhodium, ruthenium, osmium, iridium, silver and gold. Preferred catalysts may include, platinum, palladium, ruthenium and/or rhodium. The preferred metal is palladium. The noble metal is preferably present in the reaction in reduced form. The dehydrochlorination catalyst may be supplied in a reduced form, or it may be reduced in the reactor. The dehydrochlorination catalyst may contain from 0.01 to 10%, for example 0.1-5% (preferably 0.3 to 2%) of noble metal by weight based on the weight of the total catalyst.

The hydrochlorination catalyst may comprise at least one metal, or compound of a metal, selected from the group consisting of gold, mercury, palladium, silver, ruthenium, iridium, platinum, rhodium, copper, bismuth, tin, zirconium, antimony, and lead or a compound thereof. It is believed that the active form of the catalyst for hydrochlorination is a metal in an oxidation state >0. Therefore it is preferred that at least a portion of the metal in the hydrochlorination catalyst is present in a higher oxidation state than 0, i.e. a positive oxidation state. The hydrochlorination catalyst may contain from 0.01 to 10%, for example 0.1-5% (preferably 0.3 to 2%) of metal by weight based on the weight of the total catalyst. Alternatively, the hydrochlorination catalyst may be non-metallic. Non-metallic catalysts for the hydrochlorination of acetylene may contain at least one non-metallic compound containing B, N, O, S or P. The use of a non-metallic catalyst for hydrochlorination may be beneficial because the non-metallic catalysts may be resistant to some deactivation mechanisms when used at high temperatures. Examples of non-metallic catalysts which may be suitable include a catalyst support, such as carbon, doped with a nitrogen-containing compound such as melamine, urea, pyrrole, pyridine, pyrimidine, or purine; an O-containing compound such as an acid or hydrogen peroxide, a B-containing compound such as boric acid, a S-containing compound such as thiourea or a thiol or a P-containing compound such as a phosphine, phosphite, phosphate or pyrophosphate.

One type of suitable hydrochlorination catalyst comprises gold, or a compound of gold, on a solid catalyst support. Suitable catalysts are described, for example, in WO2013/008004 and in WO2010/055341, the contents of each of which are incorporated herein by reference. The active catalytic gold species is believed to comprise gold in a positive oxidation state, such as $Au^{3+}$ and $Au^{1+}$, although some of the gold present may be in the form of metallic gold ($Au^0$). Suitable gold-containing catalysts may comprise a complex of gold, for example gold complexed with a thiosulphate compound or in the form of a tetrachloroaurate ion. Suitable gold catalysts may be considered to comprise gold particles having a core comprising metallic gold and a shell or surface layer comprising higher oxidation state gold species including $Au^{3+}$. The shell need not be complete, but preferably all or substantially all the exposed surface of the particle has the surface higher oxidation state gold species; for example if the metallic gold is partially surrounded by support, the "shell" may extend only over the exposed particle surface. $Au^{3+}$ need not be the only higher oxidation state gold species present in the shell, and $Au^{1+}$ may also be present, for example. When the hydrochlorination catalyst contains gold, it may contain from 0.01-10% of gold, by weight of the total catalyst, especially 0.01-5%, for example 1% such as 0.1-1%, especially 0.05-0.5% of gold, by weight.

The hydrochlorination catalyst may comprise, in addition to the metal or metal compound: sulphur, a compound of sulphur, a nitrogen-containing compound, trichloroisocyanuric acid, a metal dichloroisocyanurate, a hydrocyanate, a halogen or halide, especially a chloride. The hydrochlorination catalyst or the dehydrochlorination catalyst may comprise an additive such as platinum, palladium, silver, a lanthanide, nickel, iron, cobalt, copper, lanthanum, cerium, lithium, sodium, potassium, rubidium, caesium, magnesium, calcium, strontium, barium or iodine. The additive may be present as a promoter or may have another function in the catalyst or its preparation. For example, some metals, such as calcium, are believed to inhibit the formation of carbon deposits on the catalysts and can therefore be used to help maintain the activity of the catalyst over a period of time. Therefore, even if the presence of an additive does not increase the activity of a catalyst in the short-term it may be regarded as a promoter if it reduces the tendency of a catalyst to deactivate during its use in a reaction or has another beneficial effect on the practical use of the catalyst such as enhancing catalyst selectivity for example.

The catalysts may be supported on any suitable support. The hydrochlorination catalyst and the dehydrochlorination catalyst may be supported on the same type of support or each on a different type of support. Catalyst supports may include alumina, particularly transition aluminas, silica, silica-alumina, zeolite, magnesia, zirconia, titania and carbon, including carbon nanotubes, carbon nanofibres, graphite and modified supports, such as nitrogen-, phosphorus- or sulphur-doped carbon. For example, the support may be modified using a nitrogen compound such as urea. A carbon support preferably includes an active carbon. Active carbon support materials are well known. Suitable carbon materials may be formed from the pyrolysis of wood, coal, nut shells, coconut shells, husks, coir, peat or other carbonaceous sources. A synthetic carbon may be used. The carbon is preferably an activated carbon, activated for example by steam, acid, or otherwise chemically activated. Preferred carbon supports include a high surface area activated carbon, preferably of surface area greater than 300 $m^2/g$, such as a 1300 $m^2/g$ carbon extrudate or granule. Carbon extrudates are available as "high purity" or "ultra-high purity" grades commercially and such grades are typically acid washed to remove impurities. A combination of metal oxide and carbon may also be used as a catalyst support.

The support may take the form of a powder, granules, pellets or other shapes, such as spheres, tablets, cylinders, rings, lobed cylinders, miniliths, monolith or any other suitable shape. An extruded pellet or cylinder is a particularly convenient form for the catalyst support. Alternatively the catalyst in the form of a powder may be included in a coating formulation and coated onto a reactor wall or shaped substrate such as a monolith or reactor insert, such as a shaped structure. One preferred form of catalyst support comprises a plurality of shaped units in the form of cylinders, spheres or lobed cylinders each having a diameter of 1-10 mm, or, more preferably a diameter in the range 3-5 mm. In the case of a cross-section shape having a non-uniform diameter, such as a lobed cylinder, the diameter is an average diameter. The catalyst shapes may include channels and holes. Such catalyst support shapes are commercially available and may be made by extrusion, tabletting or by other methods, such as additive layer manufacturing.

Catalysts may be prepared using a variety of catalyst preparation techniques known generally in the art, for example impregnation, preferably using incipient wetness methods, deposition, precipitation and combinations of these. The dehydrochlorination catalyst may be made by combining a solution of a soluble compound of the noble metal with the support by known methods in the art of catalyst manufacture. Suitable metal compounds include nitrates, halides, tetrammine complexes, amongst others. The noble metal may be precipitated in the presence of the support, for example by adding an alkaline precipitant such as sodium hydroxide, sodium carbonate or ammonium hydroxide, for example. Alternatively the noble metal salt solution may be impregnated into the pores of the support material, optionally followed by drying. Optionally the metal compound on the support may be calcined. Optionally a reduction step may be used to convert the noble metal species present in the dried or calcined catalyst to elemental metal. The reduction may be carried out by treatment with a hydrogen-containing gas or by means of a wet reducing agent such as hydrazine. The catalyst may be reduced "in situ" i.e. in the reactor before or during the reaction.

The hydrochlorination catalyst may be made by any suitable preparation method, including those described above. The metal compound of a metallic hydrochlorination catalyst is normally not reduced to the elemental metal. The metal compound may be subjected to an alternative treatment, for example a pre-treatment with HCl. Such a pre-treatment may be carried out in the reactor or ex-situ. When the hydrochlorination catalyst comprises a compound of gold, for example, the catalyst may be made by impregnating the support with a solution of gold, for example a solution in aqua regia (a mixture of hydrochloric acid and nitric acid). Alternatively, we have found that an effective catalyst may be made by impregnating a catalyst support with a complex of the active metal, for example a gold complex. The gold complex may, for example be a complex of gold with a sulphur-containing ligand or a nitrogen-containing ligand. Such complexes may be soluble in readily available solvents, such as water, which present few environmental hazards. Suitable solutions for impregnation include aqueous solutions of metal sulphates, sulphonates, thiosulphates, thiocyanates, thiourea, thionyl chloride, thiopropionic acid and thiomalic acid, cyanates, trichloroisocyanuric acid complexes or a metal dichloroisocyanurate.

Impregnation methods may be carried out by the incipient wetness or "pore-filling" protocol, in which the amount of solution used is calculated to be just fill the pores of the support. Typically, using an incipient wetness method of impregnation, the volume of solution used is 100%±up to about 20% of the measured (or calculated) pore volume of the support. The support is usually mixed with the solution by tumbling or the solution may be added, e.g. drop-wise or by spraying, to an agitated bed of support over a period of time. As an alternative, the catalyst support may be impregnated with the solution containing a gold compound or gold complex and any other required compounds, such as a sulphur-containing compound or trichloroisocyanurate, using an excess volume of solution so that the gold, sulphur-compound and/or trichloroisocyanurate is deposited on the catalyst support by absorption or by ion-exchange reactions. As a further alternative, deposition-precipitation methods may be used. The person skilled in the art of catalyst manufacture is acquainted with such methods of preparing catalysts by impregnation of support materials with a solution of active metal compounds.

The amount of the gold or other metal compound in the impregnating solution is calculated to provide the required amount of gold in the finished catalyst. The gold is normally present in the catalyst as a layer. Typically, in a 3 mm catalyst particle for example, the gold is present in a layer of up to about 300 microns thick, extending inwardly from the surface of the catalyst support. However the gold may be uniformly distributed throughout the catalyst particle.

A non-metallic hydrochlorination catalyst may be prepared by impregnating a porous catalyst support with the selected non-metallic compound, for example a compound containing B, N, O, S or P, optionally dissolved in a suitable solvent. The impregnated catalyst support is then separated from any supernatant liquid present, then optionally dried and optionally heat-treated, for example to a temperature in the range from 200-1000° C. The preparation, or at least some steps, may be carried out under a non-oxygen containing atmosphere (e.g. a nitrogen atmosphere). When using carbon supports, it is greatly preferred to carry out any heating steps under an inert (non-oxidising) atmosphere.

As an example, a useful catalyst which may function as the hydrochlorination catalyst in the method of the invention may be made by impregnating a particulate carbon support with an aqueous solution containing a compound of gold and a compound containing a thiosulphate ion, followed, if necessary, by separation of excess solution and then drying the impregnated material. We believe that the compound of gold and compound containing a thiosulphate ion together form a gold-thiosulphate complex.

The dehydrochlorination and hydrochlorination catalysts may be present in separate reaction vessels. The feed stream containing the EDC may be flowed through the a first vessel containing a dehydrochlorination catalyst and then the product stream from the first reaction vessel may be passed through a second reaction vessel containing the hydrochlorination catalyst. The reaction conditions, including temperature and/or pressure, may be the same in each vessel or different. The reactor may include heating means, such as a supply of steam, heating oil, a furnace etc which may be supplied in a conventional manner.

The dehydrochlorination and hydrochlorination catalyst may be present in the same vessel. A reaction vessel may contain particles of a dehydrochlorination catalyst and particles of a hydrochlorination catalyst. The particles of dehydrochlorination and hydrochlorination catalysts may be arranged in different regions of the vessel. For example, the particles of dehydrochlorination catalyst and hydrochlorination catalyst may be arranged in separate layers within the vessel. In such a case the layers may be separated by a boundary such as a metal gauze or support. The catalyst bed may be arranged such that the feed-stream contacts the dehydrochlorination catalyst before contacting the hydrochlorination catalyst. One or more layers of an inert particulate material may be present in the reaction vessel. The particles of dehydrochlorination catalyst and hydrochlorination catalyst may be mixed together to form a mixed catalyst bed. The proportions of each catalyst in the mixture may be varied in different regions of the reaction vessel.

The reaction vessel may contain a fixed bed of catalyst particles. The reaction vessel may comprise an axial flow reactor. The reaction vessel may comprise one or more reaction tubes containing a catalyst bed. One or more tubular reactors (reaction vessels) may be arranged in series or in parallel, for example as a multi-tubular reactor. The reaction vessel may be provided with heat transfer means. The reaction vessel may be provided with a temperature controller. A multi-tubular reactor may comprise a plurality of tubular reactors arranged within a reactor shell through which a heat transfer medium may be circulated. The fixed bed of catalyst may be arranged in a radial flow reactor. Various reactor designs are useful for carrying out the process of the invention. The reactors described in WO2011/048361 are examples of reactors which may be used in the process, wherein one or more catalyst carriers designed to promote flow of reactants through a catalyst bed are placed within a reaction tube. In particular embodiments, the reaction vessel preferably does not comprise or consist of a reaction system of multistage reactors with intermediate injection of cold or sub-cooled reactants between two stages of reaction.

The dehydrochlorination and hydrochlorination catalysts may be present in the same catalyst particle. In this embodiment, the noble metal and the metal or metal compound of the hydrochlorination catalyst may be supported on the same catalyst support. Such a catalyst may be made, for example, by impregnating a catalyst support particle with two solutions, each of a noble metal compound and a gold compound respectively. Alternatively a catalyst support may be impregnated with a mixed solution containing both a noble metal compound and a metal or metal compound of a hydrochlorination catalyst. As a further alternative a catalyst particle may be formed from small particles of a dehydrochlorination catalyst and small particles of a hydrochlorination catalyst by mixing together the small particles and then forming a catalyst particle from the mixture, for example by extruding a paste containing the mixture or by tabletting, granulating or pelletising the mixture. A bi-functional catalyst, containing both dehydrochlorination and hydrochlorination catalysts in the same physical particle may comprise nanoparticles of noble metal and nanoparticles of the gold, mercury, palladium, silver or copper, both supported on a support particle. Such catalysts may be made by forming the metal nanoparticles as a suspension and then absorbing them onto a solid support. A similar method may be employed by forming metal nanoparticles comprising an alloy of more than one metal. As a still further alternative the dehydrochlorination and hydrochlorination catalysts may comprise an alloy of a noble metal with gold. As a further example, a catalyst particle may comprise a dehydrochlorination catalyst (which may comprise a noble metal such as palladium for example) on a support comprising a non-metallic catalyst, such as a nitrogen-doped carbon, for example. Such a catalyst particle may thereby exhibit dehydrochlorination activity from the noble metal catalyst and hydrochlorination activity through the non-metallic catalyst, which in this example is nitrogen-doped carbon. As a further alternative, a mixed catalyst may be made by grinding together a dehydrochlorination catalyst and a hydrochlorination catalyst.

The process of the invention will be further described in the following examples.

EXAMPLE 1 (COMPARATIVE)

30 g of a commercial 0.8% palladium on carbon catalyst, from Johnson Matthey, (Pd on 3 mm extruded carbon support particles) was loaded into a 2 cm diameter glass tube, to give a bed length of about 40 cm. The tube was contained within a horizontal tube furnace. A flow of 31 ml/min of nitrogen was then initiated through the bed. The temperature of the bed was then raised to 300° C., and 1,2-dichloroethane (ethylene dichloride, EDC) was introduced into the nitrogen stream. This was achieved by passing the nitrogen stream through a metal coil heated to 120° C., EDC liquid being pumped into the coil via a GLC pump, at a flow of 0.25 ml/min. The reactor effluent was analysed by gas chromatography at different times during the reaction and the results (mass % in the effluent stream) are shown in Table 1. It can be seen that the EDC has been dehydrochlorinated to give approximately 50% VCM in the product stream, and about 0.6% acetylene. After about 400 minutes, the EDC flow was stopped, and the catalyst bed cooled under nitrogen.

TABLE 1

|  | Time (minutes) | | |
| --- | --- | --- | --- |
|  | 124 | 218 | 415 |
| VCM concentration (%) | 50.89 | 51.97 | 50.54 |
| EDC Concentration (%) | 48.54 | 47.50 | 48.91 |
| Acetylene concentration (%) | 0.57 | 0.53 | 0.55 |

EXAMPLE 2

5 g of the Pd/C catalyst nearest the outlet of the catalyst bed as described in Example 1 were removed, and replaced by 5 g of a commercial 0.6% Au/C catalyst (from Johnson Matthey). The reactor tube loaded with the layered bed of catalyst was then purged with nitrogen, heated to 300° C., and EDC introduced as described above. The results (mass % in the effluent stream) are shown in Table 2. It can be seen that there is a significant reduction in the acetylene concentration to less than 0.2%, compared with Example 1, and a corresponding decrease in EDC and increase in VCM.

TABLE 2

|  | Time (minutes) | | | |
| --- | --- | --- | --- | --- |
|  | 38 | 60 | 257 | 303 |
| VCM concentration (%) | 53.23 | 54.1 | 52.76 | 52.29 |
| EDC Concentration (%) | 46.59 | 45.72 | 47.07 | 47.54 |
| Acetylene concentration (%) | 0.18 | 0.18 | 0.17 | 0.17 |

The invention claimed is:

1. A process for the production of vinyl chloride, comprising:
    passing a feed stream comprising ethylene dichloride over a catalyst system comprising a dehydrochlorination catalyst and a hydrochlorination catalyst at a reaction temperature and reaction pressure sufficient to effect dehydrochlorination of the ethylene dichloride to produce vinyl chloride,
    wherein the feed stream contains essentially no hydrogen,
    wherein the dehydrochlorination catalyst comprises a supported noble metal catalyst that comprises at least one of platinum, palladium, ruthenium, and rhodium, and
    wherein the hydrochlorination catalyst comprises at least one metal selected from the group consisting of gold, mercury, palladium, silver, ruthenium, iridium, platinum, rhodium, copper, bismuth, tin, zirconium, antimony, lead, and compounds thereof.

2. The process according to claim 1, wherein the reaction temperature is in the range of from 150° C. to 350° C.

3. The process according to claim 1, wherein the reaction pressure is in the range of from 0 to 55 bar G.

4. The process according to claim 1, wherein acetylene is present in the feed stream.

5. The process according to claim 1, wherein the hydrochlorination catalyst comprises gold or a compound of gold on a catalyst support.

6. The process according to claim 1, wherein the hydrochlorination catalyst comprises a non-metallic catalyst.

7. The process according to claim 1, wherein the dehydrochlorination and hydrochlorination catalysts are present in separate reaction vessels.

8. The process according to claim 1, wherein the dehydrochlorination and hydrochlorination catalysts are present in the same vessel.

9. The process according to claim 8, wherein the catalyst system comprises particles of a dehydrochlorination catalyst and separate particles of a hydrochlorination catalyst present in the same reaction vessel.

10. The process according to claim 9, wherein the separate particles of dehydrochlorination and hydrochlorination catalysts are arranged in different regions of the reaction vessel.

11. The process according to claim 9, wherein the separate particles of dehydrochlorination and hydrochlorination catalysts are mixed together to form a mixed catalyst bed.

12. The process according to claim 8, wherein the dehydrochlorination and hydrochlorination catalysts are present in the same catalyst particle.

13. The process according to claim 12, wherein the hydrochlorination catalyst and the dehydrochlorination catalyst are supported on the catalyst support of the dehydrochlorination catalyst.

14. The process according to claim 13, wherein the hydrochlorination catalyst comprises a compound containing boron, nitrogen, oxygen, phosphorus or sulphur.

15. The process according to claim 1, wherein the feed stream comprises at least 80% by weight ethylene dichloride.

16. The process according to claim 15, wherein the feed stream comprises at least 95% by weight ethylene dichloride.

* * * * *